United States Patent [19]

Hao

[11] 4,164,496
[45] Aug. 14, 1979

[54] PREPARATION OF ALBUMIN USING PEG AND EDTA

[75] Inventor: Yu L. Hao, Potomac, Md.

[73] Assignee: American National Red Cross, Washington, D.C.

[21] Appl. No.: 935,922

[22] Filed: Aug. 23, 1978

[51] Int. Cl.$^2$ .............................................. C07G 7/00
[52] U.S. Cl. ................ 260/122; 260/112 B; 424/101
[58] Field of Search ............ 260/112 B, 122; 424/101

[56] References Cited

U.S. PATENT DOCUMENTS

| | | | |
|---|---|---|---|
| 2,469,193 | 5/1949 | Cohn | 260/122 X |
| 2,705,230 | 3/1955 | Reid | 260/122 |
| 2,710,294 | 6/1955 | Gerlough | 260/122 X |
| 2,765,299 | 10/1956 | Porsche et al. | 260/122 |
| 3,415,804 | 12/1968 | Polson | 260/112 R |
| 3,790,552 | 2/1974 | Johnson et al. | 260/112 R X |
| 3,992,367 | 11/1976 | Plan et al. | 260/122 |
| 4,017,470 | 4/1977 | Izaka et al. | 260/122 X |
| 4,090,977 | 5/1978 | Dubin | 424/101 X |

OTHER PUBLICATIONS

Chem. Abstracts, vol. 55, 1961, 10554c-e, Inman et al.
Chem. Abstracts, vol. 84, 1976, 22080n, Schneider et al.
Blut, 30, pp. 121–134, (1975), Schneider et al.
Vox Sang, 6, pp. 34–52, (1961), Inman et al.

*Primary Examiner*—Howard E. Schain
*Attorney, Agent, or Firm*—Holman & Stern

[57] ABSTRACT

Methods for the large scale preparation of clinical albumin are disclosed. One method includes dilution of plasma with a NaCl solution containing disodium ethylene dinitrilo tetraacetate and a stabilizer such as sodium caprylate. The resulting solution is then subjected to heating and cooling steps, followed by the addition of polyethylene glycol to precipitate impurities, with albumin remaining in the supernatant. Isoelectric precipitation is then employed to recover the desired albumin product, which is devoid of the albumin dimer. In an alternative method, ethanol is employed as the precipitating agent rather than polyethylene glycol.

2 Claims, No Drawings

PREPARATION OF ALBUMIN USING PEG AND EDTA

BACKGROUND AND SUMMARY OF THE INVENTION

The present invention relates to the preparation of albumin. More particularly, the present invention is directed to a method in which large-scale preparation of clinical albumin is facilitated. The method has the advantages of giving a significantly higher yield than prior art procedures and of requiring less than one-half the processing time of such known procedures as the Cohn procedure.

Previous large-scale procedures for the preparation of albumin have included those described by Cohn et al. in *J. Amer. Chem. Soc.* 68, 459–475 (1946) and *J. Amer. Chem. Soc.* 72, 465–474 (1950). Other procedures for the preparation of albumin have included that described by W. Schneider et al., Blut. 30: 121–134 (1975). Such prior art procedures, in general, have not resulted in satisfactory yields and have required long processing periods in order to prepare the albumin. The present invention for the preparation of albumin has the advantages of providing a significantly higher yield than the Cohn et al. procedure and of requiring less than one-half the processing time of the Cohn et al. procedure.

The present method for the preparation of albumin includes the steps of: (1) dilution of plasma in liquid form with an equal volume of an aqueous NaCl solution containing: (a) EDTA (diosodium ethylene dinitrilo tetraacetate) to break the iron-transferrin complex and possibly other metallo proteins; and (b) a stabilizer such as sodium caprylate: (2) heating the plasma-containing solution at approximately 60° C. for about 1½ hours at a pH of 6.2±0.1; (3) cooling the solution to about 10° C.; (4) precipitation of impurities of the heated solution with PEG 4000 (polyethylene glycol) at approximately 18–20% by weight concentration, leaving the albumin in the supernatant; (5) isoelectric precipitation of albumin from the PEG supernatant at a pH of about 4.6; and (6) recovering the resultant albumin which is devoid of the albumin dimer.

In the literature there is a description by Inman et al., *Vox Sang.* 6: 34–52 (1961) of a large-scale method for the purification of human transferrin. In the literature method, the use of EDTA and ethanol at low temperature is described for decreasing the solubility of transferrin during the purification of this protein. The method of the present invention includes the use of EDTA and heating, on the other hand, in order to reduce the stability of transferrin and other metallic proteins, thus effecting conformational changes which facilitate their precipitation by 20% PEG, leaving a highly purified albumin in the supernatant.

In an alternative method of the present invention, the steps include: (a) adjusting the pH of plasma in liquid form to about 6.7; (b) heating the plasma at a temperature of approximately 60° C. for about 1½ hours; (c) adjusting the pH of the plasma to about 5.7; (d) precipitating impurities from the plasma by the addition of ethanol in an amount sufficient to give a final concentration of about 40 to 44% by volume in the plasma, along with cooling of the plasma to about −5° C., with the albumin remaining in the supernatant; and (e) adjusting the pH of the supernatant to about 4.8 to precipitate albumin from the supernatant.

DESCRIPTION OF THE PREFERRED EMBODIMENTS

In the method of the present invention for preparing clinical albumin on a large scale, the method was carried out in a series of steps which are described hereinafter as Example I, with Example I being presented in the form of a flow chart.

The plasma employed should be in liquid form at a temperature such as, for example, about 5° C. The salinity of the NaCl solution should be selected so as to approximate the salinity of the plasma itself.

The amount of EDTA employed may vary, with an amount as low as about 2mM having been employed in Example I with good results.

EXAMPLE I

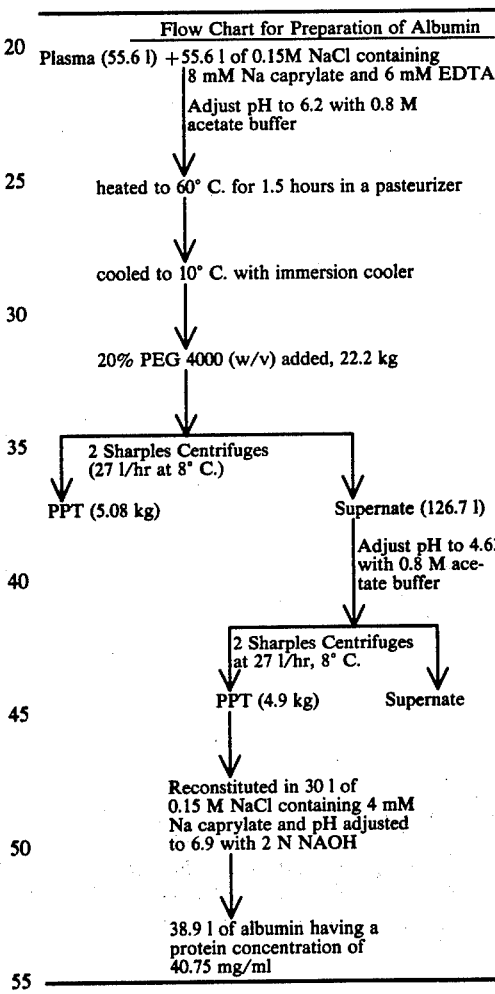

Any suitable stabilizer other than sodium caprylate may be employed, so long as the stabilizer functions to stabilize the albumin in solution. Under the conditions of Example I, from about 4mM to about 8mM of stabilizer are generally employed.

The method of the present invention results in increased yields of the desired product, in an amount of about 28.5 g/liter, for example, when the method is carried out at a pilot plant scale at MDPH (Michigan Department of Public Health) of 55 liters. In accordance with the present invention, the use of EDTA has been found to render several of the metallo proteins unstable and precipitable during the heating process. The present method has the additional feature of providing an albumin product which is devoid of the albumin dimer, the latter being invariably found in the product prepared according to currently available procedures.

In an alternative method of the present invention, preparation of clinical albumin on a large scale was carried out in a series of steps which are described hereinafter as Example II, with Example II being presented in the form of a flow chart.

EXAMPLE II

FLOW CHART FOR LARGE-SCALE PREPARATION OF CLINICAL ALBUMIN

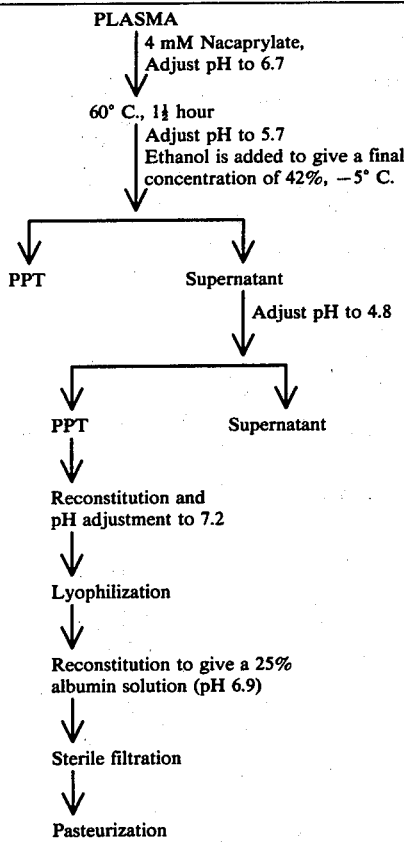

As shown in Example II, the alternative method includes the steps of: (a) adjusting the pH of plasma in liquid form to about 6.7; (b) heating the plasma at a temperature of approximately 60° C. for about 1½ hours; (c) adjusting the pH of the plasma to about 5.7; (d) precipitating impurities from the plasma by the addition of ethanol in an amount sufficient to give a final concentration of about 40 to 44% by volume in the plasma, along with cooling of the plasma to about −5° C., with the albumin remaining in the supernatant; and (e) adjusting the pH of the supernatant to about 4.8 to precipitate albumin from the supernatant. The pH may be adjusted throughout the above steps by the use of, for example, a 0.8 M acetate buffer. As further shown in Example II, the albumin obtained by the precipitation may be subjected to further steps of reconstitution, lyophilization, filtration and pasteurization to obtain the final product, with the pH being adjusted as indicated by a material such as a dilute NaOH solution.

The methods of Example I and II have been evaluated on the 55–60 liter scale and there has been obtained a yield of albumin of 28.1 grams/liter by the method of Example II. These methods compare favorably with the Cohn procedure which produced albumin in the amount of from 22 to 23 grams/liter.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. A method for the preparation of albumin comprising:
   (a) diluting plasma in liquid form with an equal volume of a NaCl solution containing disodium ethylene dinitrilo tetraacetate and a stabilizer;
   (b) adjusting the pH of the plasma solution resulting from step (a) to about 6.2;
   (c) heating the plasma solution from step (b) at a temperature of approximately 60° C. for about 1½ hours;
   (d) cooling the plasma solution to about 10° C.;
   (e) precipitating impurities from the solution with polyethylene glycol at a concentration of about 18–20% with the albumin remaining in the supernatant;
   (f) isoelectrically precipitating albumin from said supernatant at a pH of about 4.6; and
   (g) recovering the albumin product.

2. The method of claim 1 wherein said stabilizer is sodium caprylate.

* * * * *